(12) United States Patent
Hoech-Guldberg et al.

(10) Patent No.: US 7,067,278 B1
(45) Date of Patent: Jun. 27, 2006

(54) NUCLEIC ACID ENCODING PIGMENT PROTEIN FROM CORAL TISSUE

(75) Inventors: Ove Hoech-Guldberg, Queensland (AU); Sophie Dove, Queensland (AU)

(73) Assignee: The University of Sydney, Sydney (AU)

( * ) Notice: Subject to any disclaimer, the term of this patent is extended or adjusted under 35 U.S.C. 154(b) by 0 days.

(21) Appl. No.: 09/890,463

(22) PCT Filed: Feb. 2, 2000

(86) PCT No.: PCT/AU00/00056

§ 371 (c)(1),
(2), (4) Date: Nov. 9, 2001

(87) PCT Pub. No.: WO00/46233

PCT Pub. Date: Aug. 10, 2000

(30) Foreign Application Priority Data

Feb. 2, 1999 (AU) .................................. PP8463

(51) Int. Cl.
*C12P 21/06* (2006.01)
(52) U.S. Cl. .................. 435/69.1; 435/69.1; 435/6; 435/7.1; 435/320.1; 435/252.3; 435/325; 536/23.1; 536/23.5; 536/24.3; 530/350; 424/59
(58) Field of Classification Search .............. 435/69.1, 435/6, 7.1, 320.1, 252.3, 325; 536/23.1, 536/23.5, 24.3; 530/350; 424/59
See application file for complete search history.

(56) References Cited

OTHER PUBLICATIONS

Gurskaya et al., FEBS Letters, vol. 507 (1), pp. 16-20, 2001.*
Gurskaya et al., Alignment: GenEmbl database, Accession No. AF383156, Nov. 5, 2001.*
Tuddenham et al., Nucleic Acids Research, vol. 22 (17), pp. 3511-3533, 1994.*
Verploegen et al., Blood, vol. 96 (9), pp. 3215-3223, 2000.*
Norris et al., Plant Molecular Biology, vol. 24, pp. 673-677, 1994.*
Matz et al, *Nature Biotechnology*, 17:969-973 (1999).
Dove et al, *Biological Bulletin*, 189:288-297 (1995).

* cited by examiner

*Primary Examiner*—Jon Weber
*Assistant Examiner*—Hope Robinson
(74) *Attorney, Agent, or Firm*—Sughrue Mion, PLLC

(57) ABSTRACT

Pigment protein derived from corals (PPCT), and polynucleotide molecules encoding the pigment protein are disclosed. The pigment protein is capable of emitting fluorescence upon irradiation by incident light, wherein maximal absorbance of the incident light is in the range of 320–600 nm, and maximal fluorescence emission is in the range of 300–700 nm. Uses of the pigment protein are also disclosed, especially as a tissue marker, fluorescent marker or general dyestuff.

20 Claims, 10 Drawing Sheets

DEGENERATIVE OLIGOMER (30-MER):

TCCGTTATCGCTAAACAGATGACCTACAAA       (SEQ ID NO: 15)

Figure 1

BASPOC3.pep

```
  1  SVIAKQMTYK VYMSGTVNGH YFEVEGDGKG KPYEGEQTVR LAVTKGGPLP
 51  FAWDILSPQC QYGSIPFTKY PEDIPDYVKQ SFPGRYTWER IMNFEDGAVC
101  TVSNDSSIQG NCFIYHVKFS GLNFPPNGPV MQKKTQGWEP NTERLFARDG
151  MLIGNNFMAL KLEGGGHYLC EFKSTYKARK PVKMPGYHYV DRKLDVTNHN
201  KDYTSVEQRE ISIARKPLVA CCFFRVKSRH K* (SEQ IN NO: 3)
```

In bold, differences between clones.

Figure 3

BASPOC4.pep

```
  1  SVIAKQMTYK VYMSGTVNGH YFEVEGDGKG KPYEGEQTVR LAVTKGGPLP
 51  FAWDILSPQC QYGSIPFTKY PEDIPDYVKQ SFPGRYTWER IMNFEDGAVC
101  TVSNDSSIQG NCFIYHVKFS GLNFPPNGPV MQKKTQGWEP NTERLFARDG
151  MLIGNNFMAL KLEGGGHYLC EFKSTYKAKK PVKMPGYHYV DRKLDVTNHN
201  KDYTSVEQCE ISIARKPVVA CRFFRVKSRH KYAVA* (SEQ ID NO: 4)
```

Figure 4 t7SP6BASPOC3  Length: 841
```
    1  TCCGTTATCG CTAAACAGAT GACCTACAAA GTTTATATGT CAGGCACGGT
   51  CAATGGACAC TACTTTGAGG TCGAAGGCGA TGGAAAAGGA AAGCCTTACG
  101  AGGGGGAGCA GACGGTAAGG CTGGCTGTCA CCAAGGGCGG ACCTCTGCCA
  151  TTTGCTTGGG ATATTTTATC ACCACAGTGT CAGTACGGAA GCATACCATT
  201  CACCAAGTAC CCTGAAGACA TCCCTGACTA TGTAAAGCAG TCATTCCCGG
  251  GGAGATATAC ATGGGAGAGG ATCATGAACT TTGAAGATGG TGCAGTGTGT
  301  ACTGTCAGCA ATGATTCCAG CATCCAAGGC AACTGTTTCA TCTACCATGT
  351  CAAGTTCTCT GGTTTGAACT TTCCTCCCAA TGGACCTGTT ATGCAGAAGA
  401  AGACACAGGG CTGGGAACCC AACACTGAGC GTCTCTTTGC ACGAGATGGA
  451  ATGCTGATAG GAAACAACTT TATGGCTCTG AAGTTAGAAG GAGGTGGTCA
  501  CTATTTGTGT GAATTCAAAT CTACTTACAA GGCAAGGAAG CCTGTGAAGA
  551  TGCCAGGGTA TCACTATGTT GACCGCAAAC TGGATGTAAC CAATCACAAC
  601  AAGGATTACA CTTCCGTTGA GCAGCGTGAA ATTTCCATTG CACGCAAACC
  651  TTTGGTCGCC TGCTGTTTTT TCAGAGTCAA ATCAAGGCAC AAATAAGCAG
  701  TGGCGTAAAA AACGTAGATT CTGATTTTAG CTTAGAGAAG TAGGAACGAA
  751  GAAGTGTAGA CAACCTTCAA TGATTAAACT TTTGAAAACA ACSCCAAAAA
  801  AAAAAAAAAA AAAAAAAAAA AAAAAGCGGC CGCTCGAATT A  (SEQ ID NO: 5)
```

663 either A or C
In bold differences

Figure 5

T7SP6BASPOC4  Length: 841  (today)  Check: 7145  ..

```
  1 TCCGTTATCG CTAAACAGAT GACCTACAAA GTTTATATGT CAGGCACGGT
 51 CAATGGACAC TACTTTGAGG TCGAAGGCGA TGGAAAAGGA AAGCCTTACG
101 AGGGGGAGCA GACGGTAAGG CTGGCTGTCA CCAAGGGCGG ACCTCTGCCA
151 TTTGCTTGGG ATATTTTATC ACCACAGTGT CAGTACGGAA GCATACCATT
201 CACCAAGTAC CCTGAAGACA TCCCTGACTA TGTAAAGCAG TCATTCCCGG
251 GGAGATATAC ATGGGAGAGG ATCATGAACT TTGAAGATGG TGCAGTGTGT
301 ACTGTCAGCA ATGATTCCAG CATCCAAGGC AACTGTTTCA TCTACCATGT
351 CAAGTTCTCT GGTTTGAACT TTCCTCCCAA TGGACCTGTT ATGCAGAAGA
401 AGACACAGGG CTGGGAACCC AACACTGAGC GTCTCTTTGC ACGAGATGGA
451 ATGCTGATAG GAAACAACTT TATGGCTCTG AAGTTAGAAG GAGGTGGTCA
501 CTATTTGTGT GAATTTCAAAT CTACTTACAA GGCAAAGAAG CCTGTGAAGA
551 TGCCAGGGTA TCACTATGTT GACCGCAAAC TGGATGTAAC CAATCACAAC
601 AAGGATTACA CTTCCGTTGA GCAGTGTGAA ATTTCCATTG CACGCAAACC
651 TGTGGTCGCC TGCCGTTTTT TCAGAGTCAA ATCAAGGCAC AAATACGCAG
701 TGGCGTAAAA AACGTAGATT CTGATTTTAG CTTATAGAAG TAGGAACGAA
751 GAAGTGTAAA CAACCATTAA TGATTAAACT TTTGAAAACA ACGCCATAAA
801 AAAAAAAAAA AAAAAAAAAA AAAAAGCGGC CGCTCGAATT A (SEQ ID NO: 6)
```

Figure 6

SEQUENCE LISTING

<160> NUMBER OF SEQ ID NOS: 15

<210> SEQ ID NO 1
<211> LENGTH: 5
<212> TYPE: PRT
<213> ORGANISM: Acropora aspera, Acropora horrida, Montipora caliculata, Porites murrayensis, Montipora monasteriata and Porites lobata

<400> SEQUENCE: 1

Ser Val Ile Ala Lys
1               5

<210> SEQ ID NO 2
<211> LENGTH: 17
<212> TYPE: PRT
<213> ORGANISM: Acropora horrida

<400> SEQUENCE: 2

Ser Val Ile Ala Lys Gln Met Thr Tyr Lys Val Tyr Met Ser Gly Thr
1               5                  10                  15

Val

<210> SEQ ID NO 3
<211> LENGTH: 231
<212> TYPE: PRT
<213> ORGANISM: Acropora aspera

<400> SEQUENCE: 3

Ser Val Ile Ala Lys Gln Met Thr Tyr Lys Val Tyr Met Ser Gly Thr
1               5                  10                  15

Val Asn Gly His Tyr Phe Glu Val Glu Gly Asp Gly Lys Gly Lys Pro
            20                  25                  30

Tyr Glu Gly Glu Gln Thr Val Arg Leu Ala Val Thr Lys Gly Gly Pro
        35                  40                  45

Leu Pro Phe Ala Trp Asp Ile Leu Ser Pro Gln Cys Gln Tyr Gly Ser
    50                  55                  60

Ile Pro Phe Thr Lys Tyr Pro Glu Asp Ile Pro Asp Tyr Val Lys Gln
65                  70                  75                  80

Ser Phe Pro Gly Arg Tyr Thr Trp Glu Arg Ile Met Asn Phe Glu Asp
                85                  90                  95

Gly Ala Val Cys Thr Val Ser Asn Asp Ser Ser Ile Gln Gly Asn Cys
            100                 105                 110

Phe Ile Tyr His Val Lys Phe Ser Gly Leu Asn Phe Pro Pro Asn Gly
        115                 120                 125

Pro Val Met Gln Lys Lys Thr Gln Gly Trp Glu Pro Asn Thr Glu Arg
    130                 135                 140

Leu Phe Ala Arg Asp Gly Met Leu Ile Gly Asn Asn Phe Met Ala Leu
145                 150                 155                 160

Lys Leu Glu Gly Gly Gly His Tyr Leu Cys Glu Phe Lys Ser Thr Tyr
                165                 170                 175

Lys Ala Arg Lys Pro Val Lys Met Pro Gly Tyr His Tyr Val Asp Arg
            180                 185                 190

Lys Leu Asp Val Thr Asn His Asn Lys Asp Tyr Thr Ser Val Glu Gln
        195                 200                 205

Arg Glu Ile Ser Ile Ala Arg Lys Pro Leu Val Ala Cys Cys Phe Phe
    210                 215                 220

Arg Val Lys Ser Arg His Lys
225                     230

<210> SEQ ID NO 4
<211> LENGTH: 235
<212> TYPE: PRT
<213> ORGANISM: Acropora aspera

<400> SEQUENCE: 4

Ser Val Ile Ala Lys Gln Met Thr Tyr Lys Val Tyr Met Ser Gly Thr
1               5                   10                  15

Val Asn Gly His Tyr Phe Glu Val Glu Gly Asp Gly Lys Gly Lys Pro
            20                  25                  30

Tyr Glu Gly Glu Gln Thr Val Arg Leu Ala Val Thr Lys Gly Gly Pro
        35                  40                  45

Leu Pro Phe Ala Trp Asp Ile Leu Ser Pro Gln Cys Gln Tyr Gly Ser
    50                  55                  60

Ile Pro Phe Thr Lys Tyr Pro Glu Asp Ile Asp Tyr Val Lys Gln
65                  70                  75                  80

Ser Phe Pro Gly Arg Tyr Thr Trp Glu Arg Ile Met Asn Phe Glu Asp
                85                  90                  95

Gly Ala Val Cys Thr Val Ser Asn Asp Ser Ser Ile Gln Gly Asn Cys
            100                 105                 110

Phe Ile Tyr His Val Lys Phe Ser Gly Leu Asn Phe Pro Pro Asn Gly
        115                 120                 125

Pro Val Met Gln Lys Lys Thr Gln Gly Trp Glu Pro Asn Thr Glu Arg
    130                 135                 140

Leu Phe Ala Arg Asp Gly Met Leu Ile Gly Asn Asn Phe Met Ala Leu
145                 150                 155                 160

Lys Leu Glu Gly Gly Gly His Tyr Leu Cys Glu Phe Lys Ser Thr Tyr
                165                 170                 175

Lys Ala Lys Lys Pro Val Lys Met Pro Gly Tyr His Tyr Val Asp Arg
            180                 185                 190

Lys Leu Asp Val Thr Asn His Asn Lys Asp Tyr Thr Ser Val Glu Gln
        195                 200                 205

Cys Glu Ile Ser Ile Ala Arg Lys Pro Val Val Ala Cys Arg Phe Phe
    210                 215                 220

Arg Val Lys Ser Arg His Lys Tyr Ala Val Ala
225                 230                 235

<210> SEQ ID NO 5
<211> LENGTH: 841
<212> TYPE: DNA
<213> ORGANISM: Acropora aspera

<400> SEQUENCE: 5
tccgttatcg ctaaacagat gacctacaaa gtttatatgt caggcacggt caatggacac      60
tactttgagg tcgaaggcga tggaaaagga aagccttacg aggggagca gacggtaagg     120 ctggctgtca ccaagggcgg acctctgcca tttgcttggg atattttatc accacagtgt    180
cagtacggaa gcataccatt caccaagtac cctgaagaca tccctgacta tgtaaagcag    240
tcattcccgg ggagatatac atgggagagg atcatgaact tgaagatgg tgcagtgtgt    300 actgtcagca atgattccag catccaaggc aactgtttca tctaccatgt caagttctct    360 ggttttgaact ttcctcccaa tggacctgtt atgcagaaga agacacaggg ctgggaaccc    420
aacactgagc gtctctttgc acgagatgga atgctgatag gaaacaactt tatggctctg    480

```
aagttagaag gaggtggtca ctatttgtgt gaattcaaat ctacttacaa ggcaaggaag      540
cctgtgaaga tgccagggta tcactatgtt gaccgcaaac tggatgtaac caatcacaac      600
aaggattaca cttccgttga gcagcgtgaa atttccattg cacgcaaacc tttggtcgcc      660
tgctgttttt tcagagtcaa atcaaggcac aaataagcag tggcgtaaaa aacgtagatt      720
ctgattttag cttagagaag taggaacgaa gaagtgtaga caaccttcaa tgattaaact      780
tttgaaaaca acsccaaaaa aaaaaaaaaa aaaaaaaaaa aaaaagcggc cgctcgaatt      840
a                                                                     841

<210> SEQ ID NO 6
<211> LENGTH: 841
<212> TYPE: DNA
<213> ORGANISM: Acropora aspera

<400> SEQUENCE: 6
tccgttatcg ctaaacagat gacctacaaa gtttatatgt caggcacggt caatggacac       60
tactttgagg tcgaaggcga tggaaaagga agccttacg aggggagca gacggtaagg      120 ctggctgtca ccaagggcgg acctctgcca tttgcttggg atattttatc accacagtgt      180
cagtacggaa gcataccatt caccaagtac cctgaagaca tccctgacta tgtaaagcag      240
tcattcccgg ggagatatac atgggagagg atcatgaact ttgaagatgg tgcagtgtgt      300
actgtcagca atgattccag catccaaggc aactgtttca tctaccatgt caagttctct      360
ggtttgaact ttcctcccaa tggacctgtt atgcagaaga agacacaggg ctgggaaccc      420
aacactgagc gtctctttgc acgagatgga atgctgatag gaaacaactt tatggctctg      480
aagttagaag gaggtggtca ctatttgtgt gaattcaaat ctacttacaa ggcaaagaag      540
cctgtgaaga tgccagggta tcactatgtt gaccgcaaac tggatgtaac caatcacaac      600
aaggattaca cttccgttga gcagtgtgaa atttccattg cacgcaaacc tgtggtcgcc      660
tgccgttttt tcagagtcaa atcaaggcac aaatacgcag tggcgtaaaa aacgtagatt      720
ctgattttag cttatagaag taggaacgaa gaagtgtaaa caaccattaa tgattaaact      780
tttgaaaaca acgccataaa aaaaaaaaaa aaaaaaaaaa aaaaagcggc cgctcgaatt      840
a                                                                     841

<210> SEQ ID NO 7
<211> LENGTH: 18
<212> TYPE: PRT
<213> ORGANISM: Acropora aspera, Montipora caliculata and Porites
      murrayensis

<400> SEQUENCE: 7

Ser Val Ile Ala Lys Gln Met Thr Tyr Lys Val Tyr Met Ser Gly Thr
1               5                   10                  15

Val Asn

<210> SEQ ID NO 8
<211> LENGTH: 25
<212> TYPE: PRT
<213> ORGANISM: Porites lobata

<400> SEQUENCE: 8

Ser Val Ile Ala Lys Gln Met Thr Tyr Lys Val Tyr Met Ser Gly Thr
1               5                   10                  15

Val Asn Asn His Tyr Glu Phe Val Thr
```

20                  25

<210> SEQ ID NO 9
<211> LENGTH: 225
<212> TYPE: PRT
<213> ORGANISM: Discosoma sp.

<400> SEQUENCE: 9

Met Arg Ser Ser Lys Asn Val Ile Lys Glu Phe Met Arg Phe Lys Val
1               5                   10                  15

Arg Met Glu Gly Thr Val Asn Gly His Glu Phe Glu Ile Glu Gly Glu
                20                  25                  30

Gly Glu Gly Arg Pro Tyr Glu Gly His Asn Thr Val Lys Leu Lys Val
            35                  40                  45

Thr Lys Gly Gly Pro Leu Pro Phe Ala Trp Asp Ile Leu Ser Pro Gln
    50                  55                  60

Phe Gln Tyr Gly Asn Lys Val Tyr Val Lys His Pro Ala Asp Ile Pro
65                  70                  75                  80

Asp Tyr Lys Lys Leu Ser Phe Pro Glu Gly Phe Lys Trp Glu Arg Trp
                85                  90                  95

Met Asn Phe Glu Asp Gly Gly Val Val Thr Val Thr Gln Asp Ser Ser
                100                 105                 110

Leu Gln Asp Gly Cys Phe Ile Tyr Lys Val Lys Phe Ile Gly Val Asn
            115                 120                 125

Phe Pro Ser Asp Gly Pro Val Met Gln Lys Lys Thr Met Gly Trp Glu
    130                 135                 140

Ala Ser Thr Lys Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
    195                 200                 205

Thr Ile Val Glu Gln Tyr Glu Arg Thr Glu Gly Arg His His Leu Phe
    210                 215                 220

Leu
225

<210> SEQ ID NO 10
<211> LENGTH: 230
<212> TYPE: PRT
<213> ORGANISM: Discosoma sp.

<400> SEQUENCE: 10

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg

-continued

```
                85                  90                  95
Thr Ile Phe Phe Lys Asp Asp Gly Asn Tyr Lys Thr Arg Ala Glu Val
            100                 105                 110
Lys Phe Glu Gly Asp Thr Leu Val Asn Arg Ile Glu Leu Lys Gly Ile
        115                 120                 125
Asp Phe Lys Glu Asp Gly Asn Ile Leu Gly His Lys Leu Glu Tyr Asn
    130                 135                 140
Tyr Asn Ser His Asn Val Tyr Ile Met Ala Asp Lys Gln Lys Asn Gly
145                 150                 155                 160
Ile Lys Val Asn Phe Lys Ile Arg His Asn Ile Glu Asp Gly Ser Val
                165                 170                 175
Gln Leu Ala Asp His Tyr Gln Gln Asn Thr Pro Ile Gly Asp Gly Pro
            180                 185                 190
Val Leu Leu Pro Asp Asn His Tyr Leu Ser Thr Gln Ser Ala Leu Ser
        195                 200                 205
Lys Asp Pro Asn Glu Lys Arg Asp His Met Val Leu Leu Glu Phe Val
    210                 215                 220
Thr Ala Ala Gly Ile Thr
225                 230

<210> SEQ ID NO 11
<211> LENGTH: 20
<212> TYPE: DNA
<213> ORGANISM: Artificial Sequence
<220> FEATURE:
<221> NAME/KEY: misc_feature
<223> OTHER INFORMATION: PCR Primers

<400> SEQUENCE: 11
tccgttatcg ctaaacagat                                            20

<210> SEQ ID NO 12
<211> LENGTH: 20
<212> TYPE: DNA
<213> ORGANISM: Artificial Sequence
<220> FEATURE:
<221> NAME/KEY: misc_feature
<223> OTHER INFORMATION: PCR Primers

<400> SEQUENCE: 12
tttgtgcctt gatttgactc                                            20

<210> SEQ ID NO 13
<211> LENGTH: 20
<212> TYPE: DNA
<213> ORGANISM: Artificial Sequence
<220> FEATURE:
<221> NAME/KEY: misc_feature
<223> OTHER INFORMATION: PCR Primers

<400> SEQUENCE: 13
cgccactgcg tatttgtgcc                                            20

<210> SEQ ID NO 14
<211> LENGTH: 20
<212> TYPE: DNA
<213> ORGANISM: Artificial Sequence
<220> FEATURE:
<221> NAME/KEY: misc_feature
<223> OTHER INFORMATION: PCR Primers

<400> SEQUENCE: 14
```

-continued

```
ggcgaccaca ggtttgcgtg                                              20

<210> SEQ ID NO 15
<211> LENGTH: 30
<212> TYPE: DNA
<213> ORGANISM: Artificial Sequence
<220> FEATURE:
<221> NAME/KEY: misc_feature
<223> OTHER INFORMATION: PCR Primers

<400> SEQUENCE: 15
tccgttatcg ctaaacagat gacctacaaa                                   30
```

NUCLEIC ACID ENCODING PIGMENT PROTEIN FROM CORAL TISSUE

This application is a 371 of PCT/AU00/00056 filed Feb. 2, 2000, which claims priority to Australian application PP8463, filed Feb. 2, 1999.

FIELD OF THE INVENTION

The present invention relates to pigment proteins derived from corals, and particularly polynucleotide molecules encoding the pigment proteins, and uses thereof.

BACKGROUND TO THE INVENTION

There are a number of pigmented and/or fluorescent molecules which have been isolated and characterised from natural sources. Examples include apoaequorin, a single polypeptide chain isolated from the luminous jellyfish *Aequarea victoria*, green fluorescent protein (GFP) and *renilla* luciferase isolated from the *Renilla* (also called sea pansies) which belong to a class of coelenterates known as anthozoans.

The present applicant has pied pigment protein from various coral tissues (PPCT) and cloned genes encoding PPCT which have unique and useful properties.

DISCLOSURE OF THE INVENTION

In a first aspect, the invention provides an isolated polynucleotide molecule comprising a nucleotide sequence encoding a pigment protein from coral tissue (PPCT) capable of emitting fluorescence upon irradiation by incident light, wherein maximal absorbance of said incident light is in the range of 320–600 nm (preferably, 550–580 nm), and maximal fluorescence emission is in the range of 300–700 nm (preferably, 400–650 nm).

Preferably, the isolated polynucleotide molecule comprises a nucleotide sequence encoding a protein having the N-terminal amino acid sequence:

SVIAK (SEQ ID NO:1).

More preferably, the isolated polynucleotide molecule comprises a nucleotide sequence encoding a protein having the N-terminal amino acid sequence:

SVIAKQMTYKVYMSGTV (SEQ ID NO: 2).

Still more preferably, the isolated polynucleotide molecule comprises a nucleotide sequence encoding a protein having an amino acid sequence corresponding to the sequence shown hereinafter as SEQ ID NO: 3 or 4.

Even more preferably, the isolated polynucleotide molecul comprises a nucleotide sequence which has at least 80%, more preferably at least 90% and most preferably at least 95%, identity to the sequence shown hereinafter as SEQ ID NO: 5 or 6.

Most preferably, the isolated polynucleotide molecule comprises a nucleotide sequence substantially corresponding to the sequence shown hereinafter as SEQ ID NO: 5 or 6.

In a preferred embodiment of the invention, the isolated polynucleotide molecule comprises a nucleotide sequence which is capable of hybridising to the sequence shown as SEQ ID NO: 5 or 6 under high stringency conditions, and is less than 5000 nucleotides in length, although it can be less than 1000 or even 500 nucleotides in length. However, preferably, hybridising polynucleotide molecules according to the invention are at least 18 nucleotides in length.

Polynucleotide molecules according to the invention which may hybridise to the sequence shown as SEQ ID NO: 5 or 6 under high stringency conditions, include polynucleotide molecules encoding PPCT isoforms known to the present applicant which are of 221 amino acids in length. Such polynucleotide molecules include a stop codon in place of the codon encoding $Cys^{221}$ shown in SEQ ID NO: 5 or 6.

In a second aspect, the invention provides a protein comprising the N-terminal amino acid sequence:

SVIAK (SEQ ID NO:1), said protein being in a substantially purified form.

Preferably, the substantially purified protein comprises the N-terminal amino acid sequence:

SVIAKQMTYKVYMSGTV (SEQ ID NO: 2).

More preferably, the protein comprises an amino acid sequence substantially corresponding to the sequences shown hereinafter as SEQ ID NO 3 or 4.

The protein according to the present invention (PPCT) has the following characteristics:
i) Aqueous soluble protein (231–235 amino acids in length);
ii) Absorbance spectra with $\lambda_{max}$ ranging from 340–600 nm;
iii) Light induced;
iv) Mostly in the form of a dimer, though sometimes trimeric;
v) About 22% amino acid identity and about 56% amino acid similarity with green fluorescent protein (GFP);
vi) Amino acid sequence "QYG" in PPCT instead of "SYG" in GFP chromatophore position;
vii) Estimated PI=9.5; and
viii) Synthesised at high temperatures (e.g. 35° C.) and stable at higher temperatures (e.g. 40° C.).

PPCTs which absorb maximally at 560–600 nm are weakly fluorescent (excitation at 560–600 nm with emission at 600–650 nm) under all conditions. Other PPCTs absorb/excite and emit at different wavelengths. Roughly, there are four classes: Fluorescent behaviours sort PPCTs into those that fluoresce when excited at wavelengths of 300–360 nm, 420–465 nm, 480–490 nm and 550–600 nm. These molecules have emission maxima at 400–450 nm, 480–490 nm, 500–505 nm and 610–630 nm, respectively (see Table 4).

PPCT can be purified from the tissues of the following coral families: Pocilloporidae, Acroporidae, Poritidae, Faviidae, Merulinidae, Fungiidae.

Preferably, PPCT is purified from the tissue of the coral: *Acropora aspera, Acropora digitifera, Acropora horrida, Acropora formosa, Montipora monasteriata, Montipora caliculata, Pocillopora damicornis, Porites murrayensis, Porites lobata, Plesiastrea versipora* or *Seriatopora hystrix*.

More preferably, PPCT is purified from the tissue of the coral: *Acropora aspera, Acropora horrida, Montipora monasteriata, Montipora caliculata, Porites murrayensis, Porites lobata*, or *Plesiastrea versipora*.

Alternatively, PPCT can be purified from a culture of a recombinant host cell expressing PPCT from an introduced PPCT-encoding polynucleotide molecule.

In a third aspect, the invention provides a suitable vector for the replication and/or expression of a polynucleotide molecule according to the first aspect of the present invention.

The vector may be, for example, a plasmid, virus or phage vector provided with an origin of replication, and preferably a promoter fox the expression of the polynucleotide and, optionally, a regulator of the promoter. The vector may contain one or more selectable markers, for example an ampicillin resistance gene in the case of a bacterial plasmid or a neomycin resistance gene for a mammalian expression vector. The vector may be used in vitro for, for example, the production of RNA or, alternatively, for the transfection or transformation of a host cell.

A fourth aspect of the invention provides host cells transfected or transformed with the vector of the third aspect of the present invention.

Suitable host cells for cloning or expressing PPCT are prokaryote, yeast, or higher eukaryote cells.

Suitable prokaryotes include eubacteria, such as Gram-negative or Gram-positive organisms, for example, E. coli, Bacilli such as B. subtilis or B. thuringiensis, Pseudomonas species such as P. aeruginosa, Salmonella typhimurium or Serratia marcescens.

Eukaryotic microbes such as filamentous fungi or yeast are also suitable hosts for expressing PPCT. Saccharomyces cerevisiae, or common baker's yeast, is the most commonly used among lower eukaryotic host microorganisms. However, a number of other genera, species, and strains are commonly available and useful herein, such as Schizosaccharomyces pombe; Kluyveromyces hosts such as K. lactis; filamentous fungi such as Neurospora or Pencillium; and Aspergillus hosts such as A. nidulans and A. niger.

Suitable higher eukaryotic host cells can be cultured vertebrate, invertebrate or plant cells. Insect host cells from species such as Spodoptera frugiperda, Aedes aegypti, Aedes albopictus, Drosophila melanogaster, and Bombyx mori can be used. Plant cell cultures of cotton, corn, potato, soybean, tomato and tobacco can be utilised as hosts. Typically, plant cells are transfected by incubation with certain strains of the bacterium Agrobacterium tumefaciens.

Propagation of vertebrate cells in culture (tissue culture) has become a routine procedure in recent years. Examples of useful mammalian host cell lines are monkey kidney CV1 line transformed by SV40 (COS-7, ATCC CRL 1651); human embryonic kidney line (293 or 293 cells subcloned for growth in suspension culture); baby hamster kidney cells (BHK, ATCC CCL 10); Chinese hamster ovary cells/-DHFR (CHO); mouse sertoli cells, monkey kidney cells (CV1, ATCC CCL 70); human cervical carcinoma cells (HELA, ATCC CCL 2); canine kidney cells (MDCK, ATCC CCL 34), and a human hepatoma cell line (Hep G2). Preferred host cells are human embryonic kidney 293 and Chinese hamster ovary cells.

Host cells are transfected or, more preferably, transformed, with expression or cloning vectors of the invention and cultured in conventional nutrient media modified as appropriate for inducing promoters, selecting transformants, or amplifying the genes encoding the desired sequences. Transformation means introducing the DNA into an organism so that the DNA is replicable, either as an extrachromosomal element or by chromosomal integration. Depending on the host cell used, transformation is carried out using standard techniques appropriate to such cells.

In a fifth aspect, the invention provides a process for producing a protein according to the second aspect of the present invention, the process comprises that step of cultivating a host cell transfected or transformed with an (expression) vector of the third aspect of the present invention under conditions suitable for expression of the polynucleotide molecule encoding the protein, and optionally recovering the expressed protein.

Such cells can be used for the production of commercially useful quantities of the encoded protein.

Since PPCT's appear to exhibit stability at high temperatures (e.g. 35–40° C.), the process of the fifth aspect may be performed at or near optimal cultivating temperatures (e.g. 30–37° C.).

In a sixth aspect, the invention provides an oligonucleotide probe or primer, the probe or primer having a sequence that hybridises selectively to a polynucleotide molecule according to the first aspect of the present invention.

In a preferred embodiment of the sixth aspect, the oligonucleotide probe or primer comprises at least 8 nucleotides, more preferably at least 18 nucleotides, and most preferably at least 25 nucleotides.

In a further preferred embodiment, the oligonucleotide probe or primer is used as a detectable probe wherein the oligonucleotide is conjugated with a label such as a radioisotope, an enzyme, biotin, a fluorescent molecule or a chemiluminescent molecule.

In a seventh aspect, the invention consists in the use of a protein according to the second aspect as a tissue marker, fluorescent marker or general dyestuff.

It is anticipated that the protein of the invention could be used as a harmless protein-based marker for following gene expression in transformed tissues. The protein of the invention also has potential as a readily manufactured, harmless dyestuff.

In an eighth aspect, the invention provides a sunscreen formulation comprising an effective amount of a protein according to the second aspect, in admixture with a suitable pharmaceutical acceptable carrier or excipient.

In a ninth aspect, the invention provides a filter for screening UV or other wavelength(s) of incident light comprising an effective amount of a protein according to the second aspect.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, where reference is made to percentage levels of nucleotide sequence identity, those levels are as calculated by the BLAST program blastn as described by Altschul, S. F. et al., "Gapped BLAST and PSI-BLAST: a new generation of protein database search programs", Nucleic Acids Research, Vol. 25, No. 17, pp 3389–3402 (1997).

As used herein, the term "high stringency conditions" refers to conditions that (1) employ low ionic strength and high temperature for washing, for example, 15 mM NaCl/1.5 mM sodium citrate/0.1% NaDodSO$_4$ at 50° C.; (2) employ during hybridisation a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (3) employ 50% formamide, 5×SSC (750 mM NaCl, 75 mM sodium citrate), 50 mM sodium phosphate (pH 6.8), 0.1% sodium pyrophosphate, 5× Denhardt's solution, sonicated salmon sperm DNA (50 µg/ml), 0.1% SDS and 10% dextran sulfate at 42° C. in 0.2×SSC (30 mM NaCl, 3 mM sodium citrate) and 0.1% SDS.

The term "substantially corresponding" as used herein in relation to nucleotide sequences is intended to encompass minor variations in the nucleotide sequence which due to degeneracy in the DNA code do not result in a change in the encoded protein. Further, this term is intended to encompass other minor variations in the sequence which may be required to enhance expression in a particular system but in which the variations do not result in a change in the functional characteristics of the encoded protein.

The term "substantially corresponding" as used herein in relation to amino acid sequences is intended to encompass minor variations in the amino acid sequences which do not result in a change in the functional characteristics of PPCT. These variations may include conservative amino acid substitutions. The substitutions envisaged are:

G, A, V, I, L, M; D, E; N, Q; S, T; K, R, H; F, Y, W, H; and P, Nα-alkylamino acids.

In order that the present invention may be more clearly understood, preferred forms will be described with reference to the following examples and drawings.

BRIEF DESCRIPTION OF THE ACCOMPANYING FIGURES

FIG. 1 shows a nucleotide sequence of a degenerative primer useful for hybridising to genes encoding PPCT.

FIG. 2 provides an electroblot of SDS PAGE of gel filtration HPLC fractions collected for sequencing. The lanes are as follows: 1. *A. horrida*, 2. *M. caliculata*, 3. *M. monasteriata*, 4. *P. lobata*, 5. *P. murrayensis*, 6. *A. formosa*, 7. *S. hystrix*, 8. *P. damicormis*, 9. *S. pistillata*. Molecular weight markers are shown in the unmarked lanes.

FIG. 3 shows a amino acid sequence encoded by clone T7SP6BASPOC3 of FIG. 3.

FIG. 4 shows a amino acid sequence encoded by clone T7SP6BASPOC4 of FIG. 4.

FIG. 5 shows a cDNA nucleotide sequence of clone T7SP6BASPOC3 encoding PPCT from *A. aspera*.

FIG. 6 shows a cDNA nucleotide sequence of clone T7SP6BASPOC4 encoding PPCT from *A. aspera*.

Figure 8:
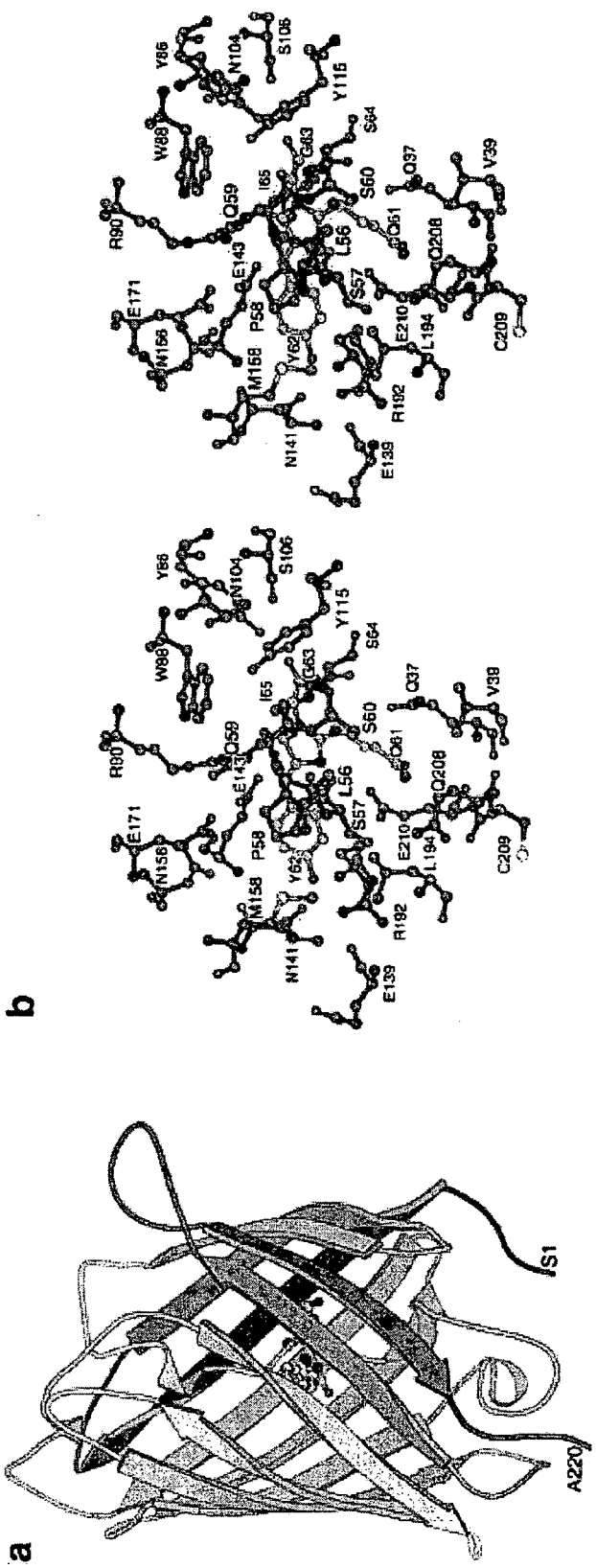

FIG. 8 provides a schematic diagram of molecular models of the principal pigment polypeptide from reef-building corals. A. MOLSCRIPT cartoon, from N-terminus to C-terminus. Arrows represent β-strands and spirals indicate helical segments. heavy atoms of the fluorophore (Q61, Y62 and G63) are shown in ball-and-stick representation. B. Charged, polar and hydrophobic side chains in the immediate vicinity are shown in ball-and-stick representation.

Figure 9:
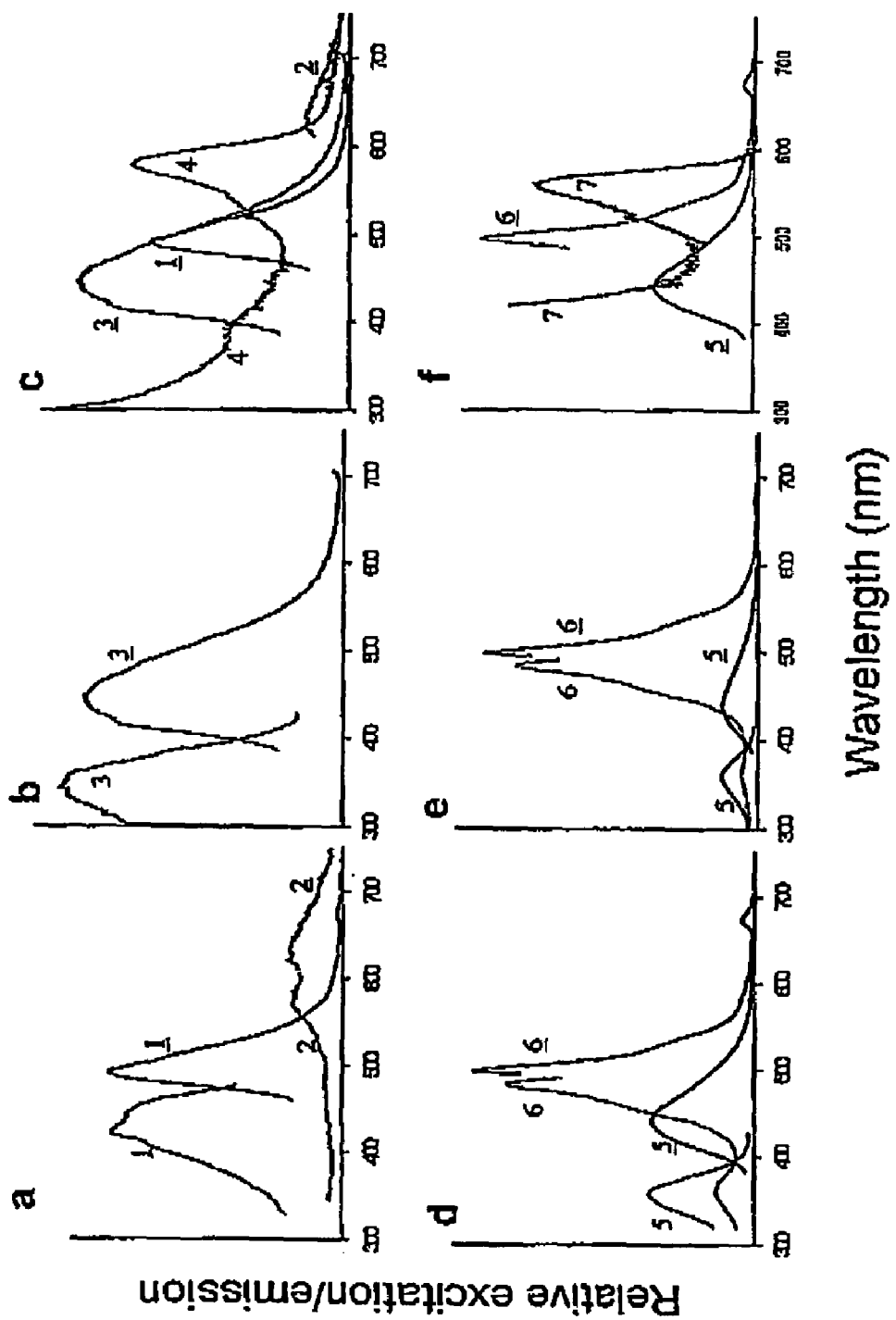

FIG. 9 shows the absorbance, excitation and emission spectra of GFP-like pigments (pociloporin) from A–C. *Acropora aspera* and D–F. *Pocillopora damicormis*. Samples taken at 27–28 min (A. and D.) and 25–26 min (B. and E.) into gel filtration run showing dominant fluorescent excitation (1–3, 5–6) and emission (1–3, 5–6) spectra. Composite absorbance (4, 7, peaks at 580 and 560 nm) and emission spectra (dashed lines) are shown in panels C. and F.

Figure 10:
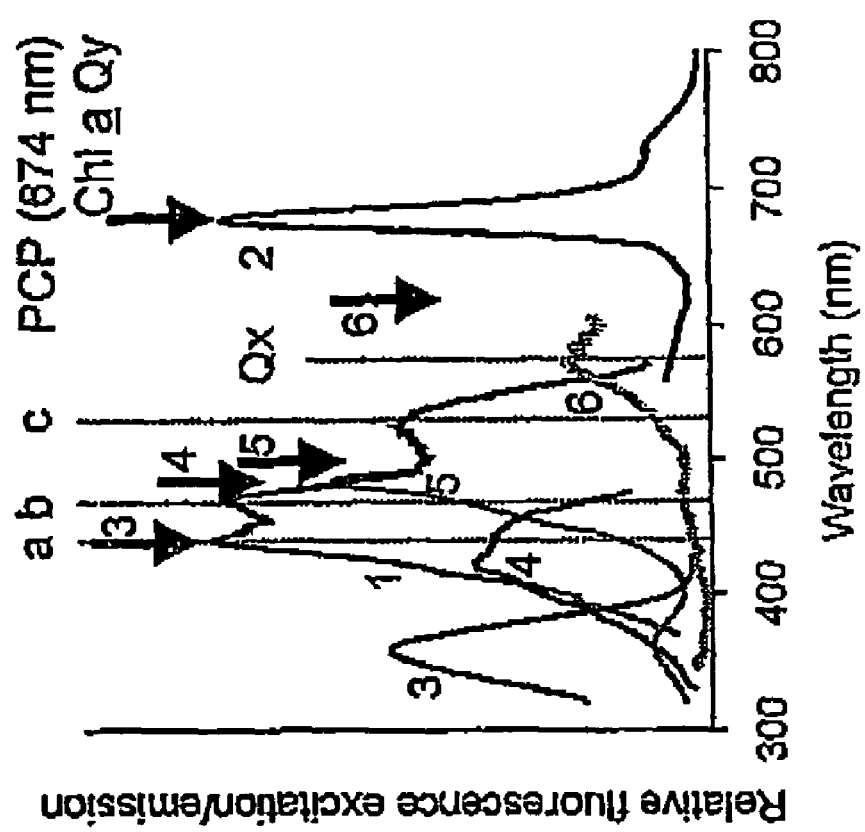

FIG. 10 shows the interaction between PPCTs and the Peridinin-chlorophyll-protein (PCP) complex of symbiotic dinoflagellates. Line 1 indicates the excitation spectra of the PCP complex of symbiotic dinoflagellates (*Acropora aspera*), which results in fluorescence emission by the isolated PCP complex at 674 nm (line 2, equivalent to the $Q_y$ Chlorophyll a transition). Lines 3, 4, 5 and 6 indicate typical excitation spectra of GFP-like pociloporins in the reef-building corals *Acropora aspera* and *Pocillopora damicormis*. Corresponding arrows indicate where emission maxima occur. Note the coupling of the emission (arrows) and excitation wavelengths of successive fluorescent pigments. Dotted lines indicate respective excitation peaks for the PCP complex and approximate position of the $Q_x$ band of Chlorophyll a. A=Chlorophyll a (441 nm), B=Peridinin (472 nm) and C=Additional vibrational band of Peridinin (525 nm).

EXAMPLE 1

General Molecular Biology

Unless otherwise indicated, the recombinant DNA techniques utilised in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1–4, IRL Press (1995 and 1996), and F. M. Ausubel et al. (Editors), Current Protocols in Molecular Biology, Greene Pub. Associates and Wiley-Interscience (1988, including all updates until present) and are incorporated herein by reference.

Gene/DNA Isolation

The DNA encoding a protein may be obtained from any cDNA library prepared from tissue believed to express the gene mRNA and to express it at a detectable level. DNA can also be obtained from a genomic library.

Libraries are screened with probes or analytical tools designed to identify the gene of interest or the protein encoded by it. For cDNA expression libraries, suitable probes include monoclonal or polyclonal antibodies that recognise and specifically bind the protein; oligonucleotides of about 20–80 bases in length that encode known or suspected portions of cDNA from the same or different species; and/or complementary or homologous cDNAs or fragments thereof that encode the same or a hybridising gene. Appropriate probes for screening genomic DNA libraries include, but are not limited to, oligonucleotides; cDNAs or fragments thereof that encode the same or hybridising DNA including expressed sequence tags and the like; and/or homologous genomic DNAs or fragments thereof. Screening the cDNA or genomic library with the selected probe may be conducted using standard procedures as described in chapters 10–12 of Sambrook et al.

An alternative means to isolate a gene encoding is to use polymerase chain reaction (PCR) methodology as described in section 14 of Sambrook et al. This method requires the use of oligonucleotide probes that will hybridise to the gene.

The oligonucleotide sequences selected as probes should be of sufficient length and sufficiently unambiguous that false positives are minimised. The actual nucleotide sequence(s) is usually based on conserved or highly homologous nucleotide sequences or regions of the gene. The oligonucleotides may be degenerate at one or more positions. The use of degenerate oligonucleotides may be of particular importance where a library is screened from a species in which preferential codon usage in that species is known. The oligonucleotide must be labelled such that it can be detected upon hybridisation to DNA in the library being screened. The preferred method of labelling is to use $^{32}$P-labelled ATP with polynucleotide kinase, as is well known in the art, to radiolabel the oligonucleotide. However, other methods may be used to label the oligonucleotide, including, but not limited to, biotinylation or enzyme labelling.

Nucleic acid having all the protein coding sequence is obtained by screening selected cDNA or genomic libraries, and if necessary, using conventional primer extension procedures as described in section 7.79 of Sambrook et al., to detect precursors and processing intermediates of mRNA that may not have been reverse-transcribed into cDNA.

Another alternative method for obtaining the gene of interest is to chemically synthesise it using one of the methods described in Fingels et al. (Agnew Chem. Int. Ed. Engl. 28: 716–734, 1989). These methods include triester, phosphite, phosphoramidite and H-Phosphonate methods, PCR and other autoprimer methods, and oligonucleotide syntheses on solid supports. These methods may be used if the entire nucleic acid sequence of the gene is known, or the sequence of the nucleic acid complementary to the coding strand is available, or alternatively, if the target amino acid sequence is known, one may infer potential nucleic acid sequences using known and preferred coding residues for each amino acid residue.

Purification Scheme
(i) Extraction of coloured pigment from coral tissue by immersing coral overnight at 4° C. in 0.6 M Potassium Phosphate buffer pH 6.65.
(ii) Gel filtration (Pharmacia, Superose HR 10/30) monitored at 280 nm & $\lambda_{max}$ eluting with Phosphate buffer (peak collection)
(iii) Desalt and lyophilise
(iv) Separate on 15% SDS-PAGE
(v) Electroblot onto PVDF using CAPS buffer
(vi) N-terminal Sequence analysis (Australian National University Sequencing Facility)

cDNA Library
Species: Blue tipped *Acropora aspera*
(i) Isolation of mRNA: Qiagen mRNA Kit (poly A+) or, more preferably, by the method described by Chomczynski and Sacchi (Anal. Biochem. 162, 156–159 (1987)).
(ii) cDNA made with SMART PCR cDNA Synthesis Kit from CLONTECH
(iii) cDNA ligated into Stratagene LambdaZapII EcoR1 cut/CIAP and packaged by Stratagene Gigapack II.

PCR out of Library
(i) Using gel purified oligomer as 5' primers and SMART PCR adaptor 3' primers—PCR amplified genes
(ii) Gel purified product ligated into pGemT easy vector (Promega) LICOR sequencing from T7 and SP6 primers and translated sequence to give the amino acid sequence.

Production of Mutants
It is anticipated that the fluorescence properties of PPCTs which are weakly fluorescent may be improved by mutagenesis. Such mutants (and the polynucleotide molecules encoding them) are to be considered as part of the present invention.

The sites for mutation can be modified individually or in series, for example by;
(i) substituting a target residue first with conservative amino acid choices and then with more radical selections depending upon the result to be achieved,
(ii) deleting a target residue, and/or
(iii) inserting residues or other ligands adjacent to the target residue.

One useful method for identification of residues or regions for mutagenesis is called "alanine scanning mutagenesis" as described by Cunningham and Wells (*Science* (1989) 244; 1081–1085). Here, a target residue or group of target residues are identified (e.g. charged residues such as Arg, Asp, His, Lys and Glu) and substituted by a neutral or negatively charged amino acid (most preferably, Ala or poly-Ala) to affect the interaction of the amino acids with the surrounding aqueous environment in or outside the cell. Those domains demonstrating functional sensitivity to the substitutions then are refined by introducing further or other mutations. Thus, while the site for introducing an amino acid sequence mutation is predetermined, the nature of the mutation per se need not be predetermined. For example, to optimise the performance of a mutation at a given site, alanine scanning or random mutagenesis may be conducted at the target codon or region and the expressed mutants are screened for the optimal combination of desired function.

EXAMPLE 2

Methods

Isolation and Purification of Pigment Proteins

Pigment proteins were purified and electrophoresed under denaturing conditions using the method described in Dove et al., Biol Bull, 189, 288–297, 1995. The resulting SDS-PAGE subunits were transferred onto PVDF paper in the presence of CAPS buffer. The 28 kD subunits isolated from five species of hermatypic corals were then sequenced by the Biomolecular Resource Facility at the Australian National University.

RNA Isolation—cDNA Library Construction—Thermocyler Conditions

Branch tips (blue) of *Acropora aspera* were collected at noon on Nov. 24, 1997 from the Heron Island reef flat and taken immediately to the research station. The total RNA from 10 tips (approximately 1 cm long) were isolated immediately and a cDNA library was made using a SMART PCR cDNA Synthesis Kit from Clontech Laboratories (Palo Alto, Calif., USA). Full length mRNA sequences of PPCT were amplified out of the library using gel purified degenerative primers made to the first 10 amino acids at the 5' end or N-terminus of the most common sequence (Table 1) and SMART PCR CDS 3' primers. This yielded a single product that was approximately 760 bp in length. Gel purified product was ligated into pGemT easy vector (Promega, Madison, Wis., USA) and sequenced using T7 and SP6 primers (2 clones, forward and reverse directions, LICOR, USA). The resultant derived proteins had 231 amino acids (POC3) and 235 amino acids (POC4) with only a few functionally similar amino acid substitutions.

Model Construction

Sequence alignment was carried out using MALIGN (Johnson et al. 1993) with the default scoring matrix derived from multiple-structure alignments and visually edited to optimise the alignment of conserved and chemically similar residues. The program MODELLER was used to generate the POC4 model, based on the template structure of the green fluorescent protein (PDB 1GFL). The initial model was iteratively refined by in-built molecular dynamics with simulated annealing protocols, to improve the structural quality as computed by PROCHECK. GRASP was used to build the molecular surface of the protein model.

Measurement of Emission and Excitation Spectra

The following gel filtration fractions were analysed for excitation and emission spectra: (i) Gel filtration fractions at intervals of one minute were collected between 25 min and 29 min that correspond approximately to trimeric through monomeric proteins of subunits ranging between 25 kD and 29 kD, (ii) Narrow gel filtration fractions collected around the wavelength of maximal absorbance for protein purification, these ranged from approximately 26 min through approximately 28 minutes depending on coral species (Table 1).

Isolation of the peridinin-chlorophyll-protein (PCP) complex from zooxanthellae. The water soluble peridinin-chlorophyll-protein (PCP) complex was isolated from zooxanthellae isolated from several corals (*Montipora digitata, Acropora aspera*) by homogenizing tissue removed from corals by using an air-brush. A symbiotic dinoflagellate rich fraction was created by spinning the homogenate at 3000 rpm for 2 min. The pellet was incubated with ice-cold phosphate buffer. PCP complexes were further purified and electrophoresed under denaturing conditions using the method described in Dove et al 1995 supra except that fractions were collected between 30–31 min.

Results and Discussion

Figure 2:
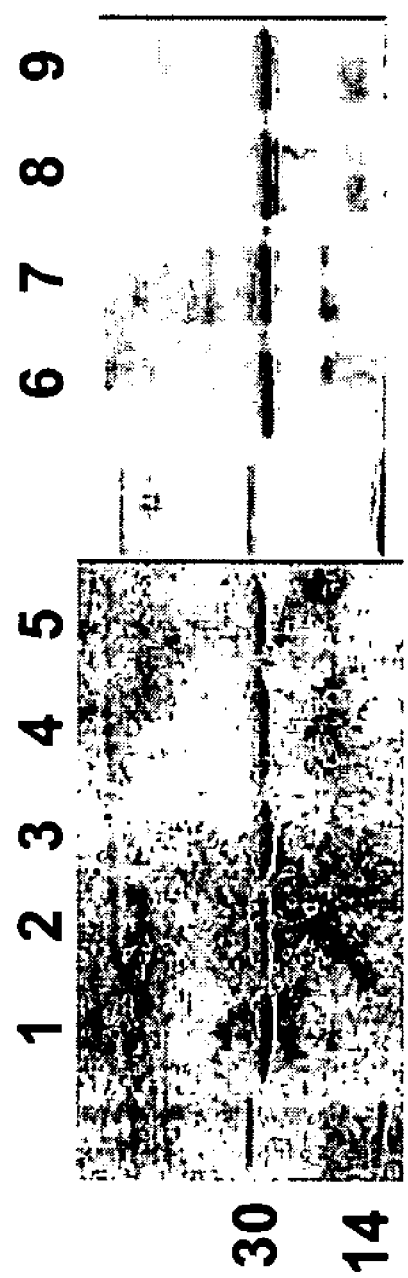
Figure 7:
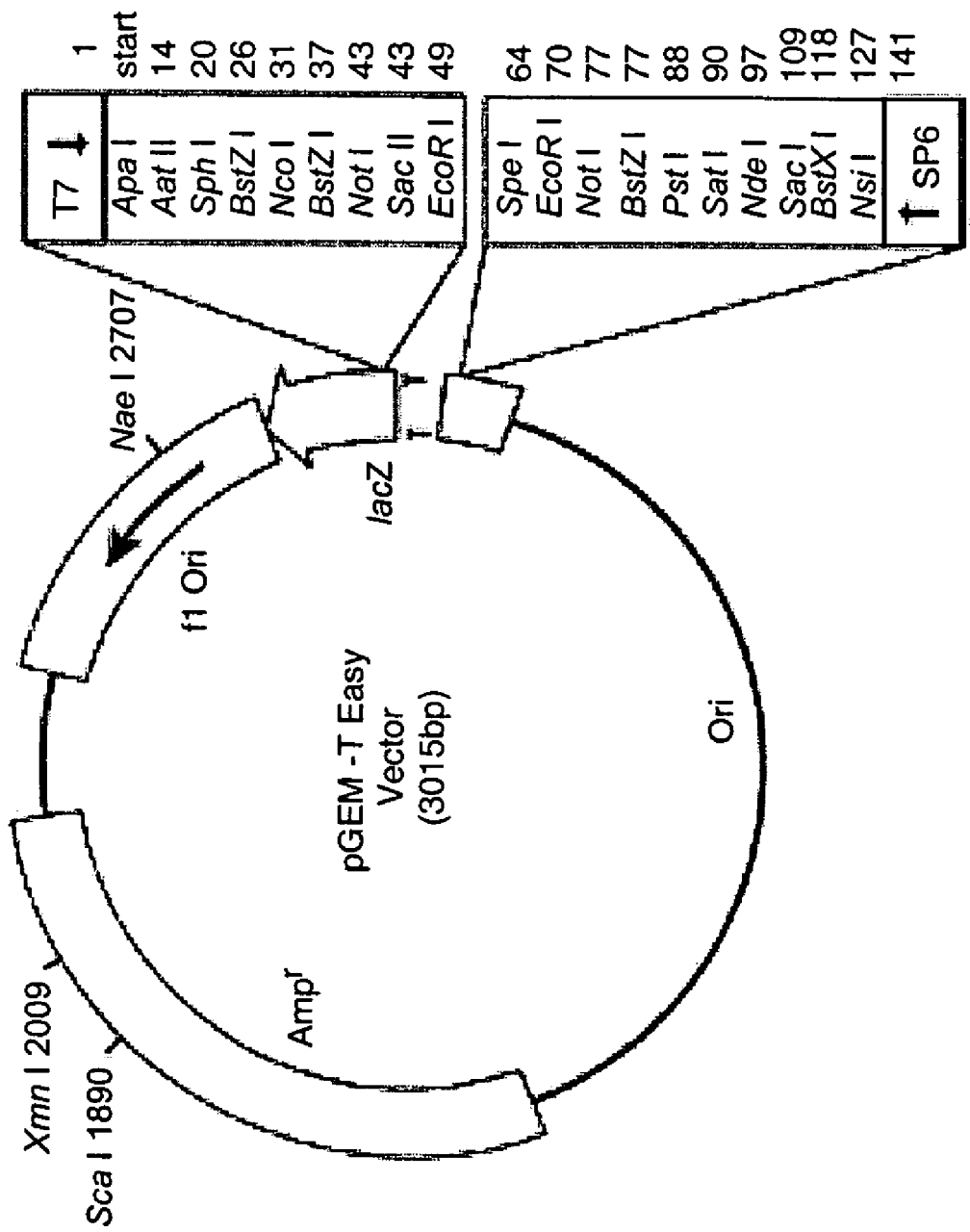
FIG. 7 shows a vector suitable for introduction and subsequent bacterial expression of cDNA encoding PPCT.

PPCT from ten species of reef-building corals were isolated. The isolated proteins had native molecular weights (approximate) that ranged from 42 to 69 kD (Table 1) and consisted of subunits that were approximately 28 kD in size (FIG. 2). The N-termini of subunits from 6 species of Acroporid and Poritid corals were sequenced, Although there were a number of background sequences in the 28 kD band, the sequence beginning with the amino acids SVIAK was common to all families (Table 1). Ion exchange chromatography using a Mono-Q column (Pharmacia, Sweden) and a variety of pH gradients and salt concentrations failed to give further resolution of the gel filtration fraction. This suggests that the surface charges on these polypeptides are very similar. In order to derive the complete sequence of the polypeptide with the common N-terminal sequence, cDNA libraries were constructed from a blue pigmented coral, *Acropora aspera*. This resulted in the successful amplification of the full length mRNA coding this protein. Amplification resulted in two clones with a few nucleic acid differences, yielding proteins of length 231 (POC3) (see FIG. 5) and 235 (POC4) (see FIG. 6), both having isoforms with stop codons at amino acid 221. Database searching matched these sequences with Green Fluorescent Protein (GFP) from the jellyfish *Aequorea victoria* (Cl. Scyphozoa). Significantly. GFP is also a dimer with a 28 kd subunit (Tsien, *Ann. Rev. Biochem.*, 67, 509–544, 1998). The alignment of POC4 with GFP and the GFP-like proteins isolated from from *Discosoma* sp. (Order Corallomorpharia, Cl. Anthozoa, Matz et al., *Nature Biotech*. 17, 969–973, 1999) showed 19.6% identity with GFP and 65.3% identity with drFP583 (Table 2). When concentrated, the narrow gel filtration fractions have approximately the same coloration as the coral from which they were derived (i.e. blue, purple or pink). The pigments observed in corals under visible light are therefore due to this family of GFP-proteins. A dimer with a 28 kD subunit matches the profile of GFP.

The construction of a 3-dimensional model revealed that the PPCT sequence can adopt the 'β-can' structure of green fluorescent protein (PDB 1GFL) (Yang et al., Nature Biotech, 14, 1246–1251, 1996), with 11 β-strands and a chromophore (composed of the modified residues Gln-61, Tyr-62 and Gly-β3) within the protein (FIG. 8B). The model shows that the chromophore is formed by the "QYG" amino acid motif. The absence of part of the N-terminal cap (see alignment in Table 2, FIG. 8A,B) in the PPCT suggests that this molecule may have a reduced ability to fluoresce as this region was found to be crucial for GFP in N-terminal truncation experiments. It is suspected that this sequence represents the high absorbance-low emission form of the pigment discussed below (excitation maxima at 570 nm, FIG. 9). The GRASP molecular surface of the PPCT model (not shown) reveals no channels, suggesting that the fluorophore is well protected from solvent. The immediate vicinity of the fluorophore appears completely shielded from bulk solvent, with 26 residues within 5 Å (listed in Table 4 and shown in FIG. 8A,B) as compared to 19 residues in GFP. This increase is partially attributable to the hydrogen bonds formed by the side chain of Gln-61. Two resonance forms have been proposed for the fluorophore, one with a partial negative charge either on the benzyl oxygen (OH) of Tyr-62 and the other with a negative charge on the carbonyl oxygen of Try-62 (part of the imidazolidone ring). Both resonance forms appear equally stabilized by Arg-192 and Arg-90 (Table 4, in bold), respectively and it is thus not possible to speculate on which form is dominant from the model. Yang et al. (1996) supra have suggested that mutation of Thr-203, Glu-222 or Ile-167 of GFP would directly affect the fluorophore, from steric and electrostatic considerations. The corresponding residues in PPCT, Arg-192, Glu-210 and Met-158, are all located in the vicinity of the fluorophore, suggesting that these are critical residues for the function of the protein. Of special importance is the presence of tryptophan residues within the "β-can" structure; Trp-88 (corresponding to Asn-94 of GFP), within van der Waals contact of the fluorophore, with Trp-53 and Trp-138 (10.8 Å and 6.7 Å, respectively) from the fluorophore. The latter, aligning with Trp-57 (13 Å in WT; Yang et al. (1996) supra) and Tyr 145 of GFP, possibly contribute to charge delocalization. It is suggested that these tryptophans are important in stabilizing and protecting the PPCT from ultraviolet radiation, which adds to its potential function under high levels of solar radiation (see below). The model structure also explains the unusual stability of PPCTs, that are expressed in shallow water environments that may exceed 35° C. as opposed to GFP with a maximum at 25° C.

Examination of the fluorescence of native PPCT from ten species of reef-building corals revealed a broad range of fluorescent behaviour which was similar to that seen in both native and mutant GFPs (Tsien et al., Biochem., 67, 509–544, 1998). Fluorescence behaviours roughly sort molecules into those that fluoresce when excited at wavelengths of 300–360 nm, 420–465 nm, 480–490 nm and 550–600 nm (Table 4). These molecules had emission maxima at 400–450 nm, 480–490 nm, 500–505 nm and 610–630 nm respectively. The group of molecules that absorb in the 550–600 nm range and emit in the 610–630 nm range have very low intensity fluorescence as can be seen from the high absorbance reading in this range for narrow gel filtration fractions (and high protein content), and their comparatively low fluorescence (FIG. 9). There were also quite substantial differences between species with respect to the types of PPCTs that were present in each coral species. PPCT derived from the blue branch tips of the Acroporid coral *Acropora aspera*, for example, fluoresced under both UVA and visible light and showed three distinct excitation maxima of 340 nm, 420 nm and 576 nm (FIG. 9 A,B). Excitation at these wavelengths led to fluorescent emissions at 445 nm (blue), 490 nm (blue-green) and 630 nm (orange-red, weak) respectively. If HPLC samples were taken at 25–26 min into a run, PPCT with an excitation maximum of 340 nm dominated while PPCTs with excitation maxima of 420 nm and 576 nm dominated samples taken at 26–27 min. Several types of PPCT were found within the tissues of *Acropora aspera*, with some forms having a greater potential to form homo, possibly hetero, dimers or trimers than others. The different elution times were also seen with PPCTs from all other species. GFP and mutants have single (major, excluding shoulders) excitation and emission maxima, further strengthening the case that each pair of excitation and emission spectra found represent individual PPCTs.

The bright colours of reef-building corals are consequently due to a combination of the absorptive and fluorescent properties of one or more GFP-like pocilloporins. For example, the blue colour of the branch tips of *Acropora aspen* is due to strong absorbance in the green to orange sections of visible spectra (peak absorbance=580 nm, and no absorbance at wavelength longer than 650 nm) and substantial blue fluorescence emission (FIG. 9C). In purple species, the absorbance maxima shift slightly away from the red end of the spectra (Table 3), but strong blue fluorescence at excitations of approximately 340 nm and/or 420–465 nm is retained. Pink coral species like *Pocillopora damicornis* (FIG. 9F), on the other hand, have PPCTs that have peak absorbance at 560 nm and no absorbance beyond 600 nm. In this case, mostly yellow and red light is transmitted and reflected back by the underlying white coral skeleton and blue fluorescence arising from excitation at 358 nm or 484 nm is relatively weak or is non-existent. Many corals are highly fluorescent at 340 nm but either do not have any visible host colour under visible light or are a luminescent green. These corals probably have the 340 nm and 420–465 nm excitation variety of GFP-like protein (green emitters) and do not have the high absorbance-low emission blue or pink varieties of PPCT described here.

Green Fluorescent Protein was discovered in the bioluminescent jellyfish (Cl. Scyphozoa) *Aequorea victoria* where it has an excitation maximum at 400 nm (shoulder at 475 nm), and an emission peak at 509 nm. In this species, GFP acts to emit green light after absorbing the blue-green light originating from the $Ca^{2+}$ activated photoprotein, aequorin (Morin et al., J. Cell Physiol., 77, 313–318). Reef-building corals are not bioluminescent. So, why do reef-building corals have fluorescent GFP-like proteins like PPCTs? The molecular properties of PPCT suggest that these proteins function in photoprotection and light harvesting as has been suggested by several authors. Different PPCTs appear to have different roles. The high absorbance-low emission varieties specifically absorb light from 550–600 nm at wavelengths which is too long for absorption by the PCP complex (410–550 nm, FIG. 13) and emit at wavelengths too short for the $Q_y$ band of chlorophylls a and c. The absorbance range of these low emitting PPCTs coincides with the $Q_x$ bands of chlorophylls a and c. The $Q_x$ band is poised to absorb scattered light due to the different dipole orientations of these chlorophylls. As the proportion of scattered light to total irradiance increases with light intensity, this particular PPCT is likely to act as a light-dependent screening pigment and reduce photoinhibition of the symbiotic dinoflagellates in high light habitats. The fact that the concentrations of the high absorbance-low emission PPCTs are correlated with PAR and not UV is further evidence of this role.

Other PPCTs convert UV radiation (down to at least 300 nm, FIG. 9a) and blue light into longer wavelengths. This suggests two additional roles of PPCT under both high and low light conditions respectively. The UV component of solar radiation has been shown to have a major and negative effect on coral and their dinoflagellate symbionts. By converting UV radiation into blue light (440–445 nm) and then (in many cases) into blue-green light (480–490 nm and 500–505 nm), UV radiation can be converted into less harmful visible radiation that can be absorbed by the PCP complex of the symbiotic dinoflagellates (FIG. 10). The PCP complex is a highly regulated light-harvesting complex that can either direct the captured energy toward the two photosystems or dump excess light energy as heat via transfers to associated carotenoids. It is striking how some of these proteins direct energy away from the Soret band at about 430 nm and into a trough in the absorbance wavelengths of the PCP complex (FIG. 10). By doing this, they clearly have a role in limiting the direct entry of light into Chlorophyll a by converting some light into that that can be absorbed by other components of the PCP complex. The behaviour of some PPCTs in converting UV light to longer wavelengths also appears poised to play a role in low light habitats. By converting non-photosynthetic UV light into blue and green light, PPCT extends the range of wavelengths over which symbiont photosynthesis can occur. Consequently, in low light habitats, the 300–360 nm and 420–465 nm forms of PPCT can function as a host based accessory pigments that increase light availability for reef-building corals that grow there. The observation that fluorescent pigment granules enhance the photosynthetic rate of deepwater corals further supports this additional role of PPCT.

TABLE 1

Size and N-terminus amin acid sequences of subunits from HPLC gel filtralion fractions.

| Coral Species | Elution time (min) | Approximate native molecular weight (Kd) | N-terminal amino acid sequences of resulting subunit (28 kD) |
|---|---|---|---|
| *Stylophora pistillata* | 27.9 | 42 | Nd |
| *Pocillopora damicormis* | 27.6 | 46 | Nd |
| *Seriatopora hystrix* | 26.9 | 57 | Nd |
| *Acropora digitifera* | 27.6 | 46 | Nd |
| *Acropora horrida* | 26.5 | 64 | SVIAKQMTYKVYMSGTV (SEQ ID NO: 2) |
| *Acropora formosa* | 26.5 | 64 | Nd |
| *Acropora aspera* | 26.4 | 65 | SVIAKQMTYKVYMSGTVN* (SEQ ID NO: 7) |
| *Montipora monasteriata* | 26.4 | 65 | SVIAK (SEQ ID NO: 1) |
| *Montipora coliculata* | 26.2 | 69 | SVIAKQMTYKVYMSGTVN (SEQ ID NO: 7) |
| *Porites murrayensis* | 26.3 | 67 | SVIAKQMTYKVYMSGTVN (SEQ ID NO: 7) |

TABLE 1-continued

Size and N-terminus amin acid sequences of subunits from HPLC gel filtration fractions.

| Coral Species | Elution time (min) | Approximate native molecular weight (Kd) | N-terminal amino acid sequences of resulting subunit (28 kD) |
|---|---|---|---|
| Porites lobata | 26.3 | 67 | SVIAKQMTYKVYMSGTVNNHYEFVT (SEQ ID NO: 8) |

Asterisk means sequence derived from cDNA

TABLE 2

Nucleotide and amino acid sequence fmRNA encoding a GFP-like protein from the reef-building coral *Acropora aspera*.

```
poc4        SVIAKQMTYKVYMSGTVNGHYFEVEGDGKGKPYEGEQTVRLTVTKGGPLPFAWDI
drfp385     MRSSKNVIKEFMREKVRMEGTVNGHRPEIEGEGEGRPYEGHNTVKLKVTKGGPLPFAWDI
gfp         MSKGEELFTGVVPILVELDGDVNGHKFSVSGEGEGDATYGKLTLKFICTT-GKLPVPWPT
Consensis       :   :      : .:.  ::**  :   ::**  .  .    : ::.  ...
```

```
poc4        XXXXXXXXXXXPFTKYPEDI--PDYXKQSFPEGXTWERIMNFEDGAVCTVSNDSSIQGNCF
drfp385     XXXXXXXXXXXVKHPADI--PDXKKESFPEGFKWERVMNFEDGGVVTVTQDSSLQDGCF
gfp         XXXXXXXXXXRYPDHMKRHDFFKSAMPEGYVQERTIFFKDDGNYKTRAEVKFEGDTL
Consensis        ..   :  :  .    :   :: :     . :  . :
```

```
poc4        IXHVKXSGLNEPPNGPVM-QKKTQGWEPNTERLFA--RDGMEIGNNFMALKLEGGG-HYL
drfp385     IXKVKFIGVNEPSDGPVM-QKKTMGWEASTKRLYP--RDGVKGEIHKALKLKDGG-HYL
gfp         VNRIELKGIDFKEDGNILGHKLEYNYNSHNVYIMADKQKNGIKVNFKIRHNIEDGSVQLA
Consensis   :  :::  :  ::     ::.         ..  :     ::::. .
```

```
poc4        CEFKSTYKAKK-PVRMPGYHYVDHKLDVTNHNKDYTS-VEQCEISIIRKPVVAWCRFFRV  (SEQ ID NO:4)
drfp385     VSFKSYMAKK-PVQLPGYYYVDSKLDITSHNEDYTI-VEQYERIERHHLFL          (SEQ ID NO:9)
gfp         DHYQQNTPIGDGPVLLPDNHYLSTQSALSKDPNEKRDHMVLLEFVTAAGIT         (SEQ ID NO:10)
Consensis    ..    .       :   :: . ..     .       .
```

TABLE 3

Maximal absorbance, and excitation and corresponding emission peaks of GFP-like proteins in reef-building corals.

| Coral Species | Colour | Absorbance (nm) | Excitation (nm) | Emission (nm) |
|---|---|---|---|---|
| Pocillopora damicormis | Pink | 560 | 358 | 440* |
| | | | 484 | 499* |
| | | | 570 | 625 |
| Serialopora hystrix | Pink | 560 | 462 | 482 |
| Acropora digitifera+ | Purple-blue | 578 (550 shoulder) | 425 570 | 490 590 |
| Acropora horrida+ | Blue | 579 | 345 420 575 | 400 485 625 |
| Acroporo aspera | Blue | 580 (550 shoulder) | 340 420–450 480 576 | 445* 490* 500 630* |
| Montipora monasteriata+ | Purple | 574–578 | 420–450 570 | 490 610 |
| Montipora caliculata+ | Purple | 579 (545 shoulder) | 420–450–465 | 485 |
| Porites lobata | | 576 (545 shoulder) | | |
| Porites murrayensis+ | Purple | 576 (545 shoulder) | 420 530 570 | 485 550 625 |
| Plesiastrea versipora | Green | 492 | 492 | 505 |

*indicate pigments profiles that are shown in FIG. 9.
+means same gel filtration fraction as that used in preparation for sequencing.

TABLE 4

Residues within 5 Å of the fluorophore, with details of atomic contacts.
Atom numbers are in accordance with PDB nomenclature.
Interactions stabilizing the resonance forms of the fluorophore are in bold.

| Protein | | Fluorophore | | Distance |
|---|---|---|---|---|
| Residue | Atom | Residue | Atom | (Å) |
| Glu-210 | OE2 | Gln-61 | CE1 | 2.5 |
| Ser-64 | N | Gly-63 | O | 2.6 |

TABLE 4-continued

Residues within 5 Å of the fluorophore,
with details of atomic contacts.
Atom numbers are in accordance with PDB nomenclature.
Interactions stabilizing the resonance forms
of the fluorophore are in bold.

| Protein | | Fluorophore | | Distance |
|---|---|---|---|---|
| Residue | Atom | Residue | Atom | (Å) |
| Arg-90 | NH2 | Tyr-62 | O | 2.7 |
| Arg-192 | NH1 | Tyr-62 | OH | 2.7 |
| Glu-210 | OE1 | Gln-61 | NE2 | 2.7 |
| Ser-57 | O | Gln-61 | N | 2.9 |
| Gln-37 | OE1 | Gln-61 | CG | 3.0 |
| Pro-58 | O | Gly-63 | N | 3.0 |
| Val-39 | CG1 | Gln-61 | OE1 | 3.3 |
| Glu-143 | OE1 | Tyr-62 | CD2 | 3.4 |
| Tyr-115 | CD2 | Gly-63 | O | 3.5 |
| Ser-106 | OG | Gly-63 | O | 3.6 |
| Asn-141 | CB | Tyr-62 | OH | 3.7 |
| Leu-194 | CD2 | Tyr-62 | CE1 | 3.7 |
| Tyr-8G | OH | Gly-63 | O | 4.2 |
| Met-158 | CE | Tyr-62 | OH | 4.2 |
| Gln-208 | CB | Gln-61 | NE2 | 4.3 |
| Glu-139 | O | Tyr-62 | OH | 4.5 |
| Asn-156 | OD1 | Tyr-62 | CE2 | 4.6 |
| Glu-171 | O | Tyr-62 | CD2 | 4.7 |
| Leu-56 | O | Gln-61 | N | 4.8 |
| Trp-58 | NE1 | Tyr-62 | O | 4.8 |
| Cys-209 | O | Gln-61 | NE2 | 5.0 |

EXAMPLE 3

POC3 and POC4 were PCR amplified out of the pGEM-EASY cloning vector using the following forward and reverse primers:
POC (FORWARD): 5'-TCC GTT ATC GCT AAA CAG AT-3' SEQ ID NO: 11)
POC3(231) (REVERSE): 5'-TTT GTG CCT TGA TTT GAC TC-3' (SEQ ID NO: 12)
POC4(235) (REVERSE): 5'-CGC CAC TGC GTA TTT GTG CC-3' (SEQ ID NO: 13)
POC4(220) (REVERSE): 5'-GGC GAC CAC AGG TTT GCG TG-3' (SEQ ID NO: 14)

Amplified sequences were gel purified and inserted into the bacterial pBAD TOPO expression vector using the pBAD TOPO TA cloning kit (Invitrogen, Carlsbad, Calif., USA), prior to transformation into ONE SHOT Competent Cells (Invitrogen, Carlsbad, Calif., USA). Reading frame and occurrence of stop codon at position AA221 in longer sequences (231 amino acids and 235 amino acids) were checked by ABI nucleotide sequencing from pBAD forward and reverse priming sites in the pBAD TOPO expression vector.

Protein expression from pBAD TOPO was regulated by optimising Arabinose concentration. Expressed proteins are purified by: (i) binding the 6× His tag that is synthesised at the C-terminus of proteins engineered to use the pBAD TOPO transcription stop codon, and (ii) by gel filtration chromatography for expressed proteins lacking the 6× His tag.

EXAMPLE 4

The ability of PPCTs to absorb light in the range of 320–700 nm, which covers UVA and UVB radiation makes them useful screening components of sunscreen formulations. Such formulations would include, for example, anefective screening amount of PPCT, optionally in admixture with a pharmaceutically acceptable carrier or excipient. Sunscreen formulations including PPCT may be produced by forming an emulsion by mixing PPCT with an agent or composition which renders the PPCT non-water soluble. Alternatively, the PPCT may be synthesised with a "tag" peptide or compound such as a long chain fatty acid (e.g. by linking the "tag" to, or near, the C-terminus of the PPCT), to render the PPCT non-water soluble and thereby capable of forming an emulsion in an aqueous carrier or excipient. Methods of acylating proteins at, for example, carboxy or amino groups (e.g. ε-amino groups) of proteins are well known in the art. The amount of PPCT present in a sunscreen formulation would generally be at least 1% by weight of the formulation. A preferred sunscreen formulation including PPCT (acylated with a fatty acid with greater than 10 carbon atoms) comprises:
  (i) about 3% cetostearyl alcohol, PEG-40 castor oil and/or sodium cetearyl sulphate,
  (ii) about 10% decyl oleate,
  (iii) about 1.5% sodium hydroxide (45% solution),
  (iv) about 0.1 to 0.5% disodiun edetate,
  (v) about 0.5% carbomer,
  (vi) about 1 to 10% acylated PPCT, and
  (vii) the balance being water.

The sunscreen formulation may also include other screening agents well known in the art for example, propyl hydroxybenzoate, dimethylaminobenzoate (PABA), phenyl salicylates, and/or octyl methoxycinnamate.

EXAMPLE 5

The ability of PPCTs to absorb light in the range of 320–700 nm also makes them useful for incorporation into various materials such as glass and polymeric materials such as perspex for use as filters for application in, for example, sunglass lenses, cameras, aquariums and greenhouses.

The absorbance range of PPCTs of 320–700 nm covers the soret band (430 nm) of chlorophyll a, but more specifically the $Q_x$ band of chlorophyll a and c (550–600 nm). The $Q_x$ band specifically absorbs scattered light associated with high light intensities. PPCTs incorporated into filters may therefore function to reduce photoinhibition of plants in high light environments. Further the ability of PPCTs to emit light at a wavelength higher than their excitation or maximal absorbance wavelength provides the possibility of transmitting across, for example, glass, the energy associated with light wavelengths which would not otherwise be transmitted. Where that energy is transferred at a wavelength in the range of photosynthetically avtive radiation (PAR), that is 400–550 nm, the use of PPCT in filters offers the possibility of generating improved growing conditions for plants, algae, corals etc. For example, use of the PPCT from A. horrida which is excited by light of 320–360 nm, would allow the absorbance of UVA light (which is not greatly transmitted by glass) to be retransmitted at the PAR wavelength of 430–450 nm.

The high-temperature tolerance of PPCT (>40° C.) enables PPCT to be readily included into, or coated onto, glass and other polymeric materials (especially polymeric materials with relatively low melting temperatures). The amount of PPCT included in glass and other polymeric materials, or alternatively included into a coating material, would generally be greater than 1% by weight.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An isolated polynucleotide molecule comprising a nucleotide sequence selected from the group consisting of: SEQ ID NO:5, SEQ ID NO:6, a nucleotide sequence having at least 80% identity with SEQ ID NO:5, a nucleotide sequence having at least 80% identity with SEQ ID NO:6, a nucleotide sequence capable of hybridizing under high stringency conditions to the complementary strand of SEQ ID NO:5, and a nucleotide sequence capable of hybridizing under high stringency conditions to the complementary strand of SEQ ID NO:6, wherein said high stringency conditions include a washing step at 50° C. in a solution comprising 15 mM NaCl and 1.5 mM sodium citrate, and wherein said polynucleotide molecule encodes a pigment protein.

2. The isolated polynucleotide molecule of claim 1, wherein said pigment protein has a maximal absorbance of incident light in a range of 320–600 nm.

3. The isolated polynucleotide molecule of claim 1, wherein said pigment protein has a maximal absorbance of incident light in a range of 550–580 nm.

4. The isolated polynucleotide molecule of claim 1, wherein said pigment protein is found in coral tissue from a coral family selected from the group consisting of: Pocilloporidae, Acroporidae, Poritidae, Faviidae, Merulinidae and Fungiidae.

5. The isolated polynucleotide molecule of claim 1, 2 or 3, wherein said pigment protein has a maximal fluorescence emission in a range of 400–630 nm.

6. The isolated polynucleotide molecule of claim 1 or 2, wherein said pigment protein has a maximal fluorescence emission in a range of 300–700 nm.

7. The isolated polynucleotide molecule of claim 1, wherein said pigment protein comprises as its N-terminal amino acid sequence SVIAK (SEQ ID NO:1).

8. The isolated polynucleotide molecule of claim 1, wherein said pigment protein comprises as its N-terminal amino acid sequence SVIAKQMTYKVYMSGTV (SEQ ID NO:2).

9. The isolated polynucleotide molecule of claim 1, 3, 7 or 8, wherein said pigment protein comprises a chromatophore region comprising the amino acid sequence: QYG.

10. The isolated polynucleotide molecule of claim 1, wherein said polynucleotide molecule encodes a protein having the amino acid sequence set forth in SEQ ID NO:3 or SEQ ID NO:4.

11. The isolated polynucleotide molecule of claim 1, wherein said polynucleotide molecule comprises a nucleotide sequence which has at least 80% identity with SEQ ID NO:5 or 6.

12. The isolated polynucleotide molecule of claim 11, wherein said polynucleotide molecule comprises a nucleotide sequence which has at least 90% identity with SEQ ID NO:5 or 6.

13. The isolated polynucleotide molecule of claim 11, wherein said polynucleotide molecule comprises a nucleotide sequence which has at least 95% identity with SEQ ID NO:5 or 6.

14. The isolated polynucleotide molecule of claim 11, wherein said polynucleotide molecule comprises the nucleotide sequence set forth in SEQ ID NO:5 or 6.

15. A vector comprising the polynucleotide molecule of claim 1, 3, 7 or 8.

16. A host cell transfected or transformed with the vector of claim 15.

17. The isolated polynucleotide of claim 4, wherein said coral tissue is selected from the group consisting of: *Acropora aspera, Acropora digitifera, Acropora horrida, Acropora formosa, Montipora monasteriata, Montipora caliculata, Pocillopora damicornis, Porites murrayensis, Porites lobata, Plesiastrea versipora* and *Seriatopora hystrix*.

18. The isolated polynucleotide of claim 17, wherein said coral tissue is from: *Acropora aspera, Acropora horrida, Montipora monasteriata, Montipora caliculata, Porites murrayensis, Porites lobata* and *Plesiastrea versipora*.

19. The host cell of claim 16, wherein the host cell is a plant cell.

20. A process for producing a pigment protein, wherein the process comprises the step of cultivating a host cell transfected or transformed with the vector of claim 16 under conditions suitable for expression of the pigment protein, and recovering the pigment protein from the host cell.

* * * * *